United States Patent [19]

Ogata et al.

[11] Patent Number: 5,773,652
[45] Date of Patent: Jun. 30, 1998

[54] METHOD FOR ISOLATION AND PURIFICATION OF S-(1,2-DICARBOXYETHYL) GLUTATHIONE

[75] Inventors: Kazumi Ogata, Toyonaka; Hideki Tsuruoka, Kawanishi, both of Japan

[73] Assignee: Senju Pharmaceutical Co., Ltd., Osaka, Japan

[21] Appl. No.: 922,464

[22] Filed: Sep. 3, 1997

[30] Foreign Application Priority Data

Sep. 4, 1996 [JP] Japan .................................. 8-233755

[51] Int. Cl.$^6$ .................................................. C07C 227/00
[52] U.S. Cl. ........................ 562/554; 562/557; 530/332; 530/344
[58] Field of Search .................... 562/554, 557; 530/332, 344

[56] References Cited

U.S. PATENT DOCUMENTS

| 4,582,801 | 4/1986 | Hamada | 435/70 |
| 5,081,149 | 1/1992 | Ohmori | 514/534 |
| 5,135,952 | 8/1992 | Ohmori | 514/547 |
| 5,212,159 | 5/1993 | Ohmori | 514/19 |
| 5,541,162 | 7/1996 | Ohmori | 514/18 |

*Primary Examiner*—Michael L. Shippen
*Attorney, Agent, or Firm*—Wenderoth, Lind & Ponack

[57] ABSTRACT

An improved method for isolating and purifying a glutathione derivative is disclosed. More particularly, the invention provides a method for isolating and purifying S-(1, 2-dicarboxyethyl)glutathione or its pharmacologically acceptable salt from a reaction mixture available upon reacting glutathione or its salt with either fumaric acid or its salt or maleic acid or its salt, which comprises a first step of converting the S-(1, 2-dicarboxyethyl)glutathione or salt thereof in the reaction mixture to the corresponding copper salt, dissolving the copper salt in an aqueous solution of acetic acid, formic acid or propionic acid, and removing the contaminant glutathione, oxidized glutathione and fumaric acid copper salts with the aid of activated carbon and a second step of dissolving or suspending the isolated S-(1, 2-dicarboxyethyl)glutathione copper salt in water and blowing hydrogen sulfide gas through the resulting aqueous solution or suspension to remove copper.

2 Claims, No Drawings

5,773,652

METHOD FOR ISOLATION AND PURIFICATION OF S-(1,2-DICARBOXYETHYL) GLUTATHIONE

BACKGROUND OF THE INVENTION

1. Field of the Invention

The present invention relates to a method for isolating and purifying a glutathione derivative. More particularly, the invention relates to a method for isolating and purifying S-(1,2-dicarboxyethyl)glutathione or a pharmacologically acceptable salt thereof.

2. Prior Art

S-(1,2-dicarboxyethyl)glutathione (hereinafter referred to briefly as DCE-GS) is an acidic tripeptide, which D. H. Calam and S. G. Waley discovered in the bovine lens (Biochem. J., 86, 226, 1963). The subsequent research of Ohmori and his coworkers revealed that DCE-GS occurs in the liver and heart as well (Archives of Biochemistry and Biophysics Vol. 279, No. 1, May 15, pp. 146–150, 1990). With regard to its pharmacological profile, the inventors of the present invention have found, thus far, that this substance has anticoagulant activity (JP Kokai S63-8337), antithrombotic activity (JP Kokai H1-79956), antiinflammatory and/or antiallergic activity (JP Kokai H3-48626), and antihistaminic and hepatoprotectant activities (JP Kokai H3-118334).

DCE-GS is readily available as glutathione and either fumaric acid or maleic acid are simply stirred together in water. However, it has been found difficult to recover DCE-GS in a high purified form from the reaction mixture on a high-production scale. The following three alternative methods have been proposed for isolating and purifying DCE-GS after completion of the reaction of glutathione with either fumaric acid or maleic acid.

One method for isolating and purifying DCE-GS comprises dissolving the reaction product free acid or salt in water, adding an organic solvent, such as an alcohol or acetone, to the solution to precipitate the product, and subjecting the precipitate to several cycles of recrystallization (JP Kokai H3-118334). This method has the disadvantage that the residual starting materials, i.e. glutathione and fumaric acid, in the solution are also coprecipitated to contaminate DCE-GS, thus making it difficult to isolate DCE-GS in pure form.

Another method comprises converting the product DCE-GS to the corresponding copper salt and recrystallizing the salt from water-ethanol (JP Kokai H3-118334). However, even by this method, it is difficult to thoroughly remove the contaminant copper salts of glutathione, oxidized glutathione, and fumaric acid contained in small amounts.

In the method proposed by Waley et al., DCE-GS is first converted to the corresponding copper salt in the same manner as above and the copper is then eliminated with oxyquinoline. However, this method, too, is incapable of thorough purification of DCE-GS and, in addition, industrially disadvantageous in that it involves the use of the expensive reagent oxyquinoline and a complicated procedure (Biochem. J. 96, 226, 1963).

Thus, it is difficult, by any of the above known methods, to isolate the product DCE-GS in a highly purified form from the reaction mixture. Therefore, the inventors of the present invention did much research to develop a commercially advantageous method for isolating and purifying DCE-GS. As a result, the inventors discovered that DCE-GS can be isolated in high purity by employing an aqueous solution of acetic acid, formic acid or propionic acid and activated carbon and have ultimately perfected the present invention.

OBJECT AND SUMMARY OF THE INVENTION

The present invention has for its object to provide an improved method for isolating and purifying DCE-GS, which is free of the above-mentioned disadvantages.

The present invention, therefore, is directed to a method for isolating and purifying S-(1,2-dicarboxyethyl) glutathione or a pharmacologically acceptable salt thereof from a reaction mixture available upon reacting glutathione or a salt thereof with either fumaric acid or a salt thereof or maleic acid or a salt thereof, which comprises a first step of converting the S-(1,2-dicarboxyethyl)glutathione or salt thereof in said reaction mixture to the corresponding copper salt, dissolving the copper salt in an aqueous solution of acetic acid, formic acid or propionic acid, and removing the contaminant glutathione, oxidized glutathione and fumaric acid copper salts with the aid of activated carbon and a second step of dissolving or suspending the isolated S-(1,2-dicarboxyethyl)glutathione copper salt in water and blowing hydrogen sulfide through the resulting aqueous solution or suspension to remove copper.

The method for isolating and purifying DCE-GS according to the present invention is now described in detail.

To start with, glutathione (or a salt thereof) and either fumaric acid (or a salt thereof) or maleic acid (or a salt thereof) are dissolved in water or an alcoholic aqueous medium and the solution is allowed to stand under warming or at room temperature for 1–2 days. By this procedure, the objective compound DCE-GS (or a salt thereof) is produced. The DCE-GS (or a salt thereof) thus produced in the reaction mixture is converted to the corresponding copper salt using copper acetate (monohydrate) or the like. After this copper salt is dissolved in an aqueous solution of acetic acid, formic acid or propionic acid, activated carbon is added to the solution to adsorb the copper salts of unreacted or excess glutathione, oxidized glutathione, and fumaric acid (in the reaction between maleic acid and glutathione, the unreacted maleic acid is transformed to fumaric acid) on the carbon and the carbon is then filtered off. Then, an alcohol or the like is added to the filtrate and the DCE-GS copper salt that separates out is recovered by filtration.

The DCE-GS copper salt thus obtained is dissolved or suspended in water and hydrogen sulfide gas is bubbled through the solution or suspension. The copper, in the form of copper sulfide, is filtered off and the filtrate is concentrated under reduced pressure. To the oily residue is added an alcohol or the like and the resulting white crystals are collected by filtration to provide DCE-GS in free acid form. When the oily residue is neutralized with an alkali metal or alkaline earth metal ion by adding the corresponding metal hydroxide, carbonate or hydrogen carbonate, the corresponding salt is obtained. This conversion to the salt may be performed after isolation of DCE-GS from the reaction mixture or in the reaction mixture. The objective compound DCE-GS or salt thereof is obtained in racemic form (since DCE-GS has asymmetric carbon within its molecule, it may occur as optical isomers). The purity of the product is not less than 98%.

The pharmacologically acceptable salt of DCE-GS includes but is not limited to salts with alkali metals such as sodium, potassium, etc. and salts with alkaline earth metals such as calcium, magnesium, etc. The salt may be such that all of the carboxyl groups of DCE-GS have formed salts or only some of them have formed salts. DCE-GS in salt form shows a longer room-temperature shelf-life than DCE-GS in free acid form.

For recrystallizing the DCE-GS copper salt in the isolation and purification method of the present invention, the DCE-GS copper salt is first dissolved in an aqueous solution of acetic acid, formic acid or propionic acid before crystallization from an alcohol. The presence of such an acid is advantageous in that the solubility of DCE-GS copper salt is increased and the crystallization of DCE-GS from the alcohol is facilitated. In the absence of said acid, the DCE-GS copper salt on recrystallization forms microfine crystals which cannot be easily collected by filtration.

In the above procedure for isolating and purifying DCE-GS, if hydrochloric acid or sulfuric acid, for instance, is used instead of acetic acid, formic acid or propionic acid for recrystallization of DCE-GS copper salt, the copper chloride or copper sulfate salt will be formed in part, so that upon addition of an alcohol for precipitation of DCE-GS copper salt, the salt mentioned just above will also be coprecipitated. In the method for isolating and purifying DCE-GS according to the present invention, hydrogen sulfide gas is bubbled through the system to remove copper in the form of copper sulfide. However, it was found that some of the hydrochloric acid or sulfuric acid, it used, remains in the filtrate after removal of copper, with the result that as the filtrate is concentrated, the concentration of the acid is increased to cause partial decomposition of the DCE-GS in the filtrate. Furthermore, when the filtrate is neutralized, the hydrochloric acid or sulfuric acid forms an inorganic salt and when an alcohol is added, it is precipitated and cannot be easily removed. In contrast, when acetic acid, formic acid, or propionic acid is used as in the present invention, the above troubles are obviated so that DCE-GS can be isolated in a highly pure form.

The preferred concentration of the aqueous solution of acetic acid, formic acid or propionic acid for use in the isolation and purification method of the present invention for DCE-GS is invariably about 1–50 v/v %.

In the method for isolating and purifying DCE-GS according to the present invention, activated carbon is used for removing the copper salts of unreacted or excess glutathione or oxidized glutathione and fumaric acid. It has been found that without the aid of activated carbon, the starting glutathione and fumaric acid cannot be removed even by several cycles of recrystallization. This is because the copper salts of glutathione and fumaric acid are less soluble than DCE-GS copper salt. The quantity of activated carbon for use in the method for isolating and purifying DCE-GS according to the present invention with respect to S-(1,2-dicarboxyethyl)glutathione copper salt is preferably about 5–20 w/w %.

EXAMPLES

The following examples are further illustrative of the present invention.

Example 1

Synthesis of S-(1,2-dicarboxyethyl)glutathione trisodium salt

In a 300 ml conical flask, 9.5 g of sodium hydroxide was dissolved in 200 ml of water, and 12.75 g (0.11 mol) of fumaric acid and 30.7 g (0.1 mol) of glutathione were added. The flask was stoppered hermetically and the contents were agitated at 50° C. for 4 hours.

To this reaction mixture were added 50 ml of acetic acid and 22.0 g (0.1 1 mol) of copper acetate (monohydrate) with stirring. To the resulting solution was added about 3 g of activated carbon and the mixture was stirred for 30 minutes and, then, filtered. The carbon was washed with a small quantity of water and the filtrate and washes were combined. After cooling, 1 L of methanol was added en bloc. The mixture was stirred until it became homogeneous and the precipitated light-blue copper salt was recovered by filtration, rinsed with methanol, and dried.

Then, for recrystallizing the copper salt, it was dissolved in 400 ml of 10 v/v % aqueous solution of acetic acid and following addition of about 3 g of activated carbon, the mixture was stirred for 20–30 minutes. The carbon was then filtered off and 1 L of methanol was added en bloc to the cooled filtrate. The copper salt that separated out was recovered by filtration and rinsed with methanol. The copper salt was recrystallized again in the same manner as above to provide 40 g as copper salt.

This copper salt was dissolved (partially remaining undissolved) in 800 ml of water and hydrogen sulfide gas was bubbled through the solution with stirring. The resulting copper sulfide was filtered off and the filtrate was concentrated under reduced pressure at a temperature not exceeding 40° C. The residual syrup was dissolved in 200 ml of water, followed by dropwise addition of 10% sodium hydroxide to adjust the solution to pH 7.4. The mixture was concentrated at 40° C. and the residual syrup was crystallized from ethanol. After cooling, the crystal crop was recovered by filtration and recrystallized from water-ethanol. The crystals thus obtained were dried in vacuo at 40° C. to provide 34 g (yield 65.8%) of the objective compound as white powdery crystals.

Elemental analysis for $C_{14}H_{18}O_{10}N_3SNa_3 \cdot 1.5H_2O$ (516.366) Calcd. (%): C, 32.56; H, 4.10; N, 8.14 Found (%): C, 32.67; H, 4.26; N, 8.13

By the isolation and purification technology of the present invention, DCE-GS or a salt thereof can be isolated in high purity from the reaction mixture available upon reacting glutathione or a salt thereof with fumaric acid (or a salt thereof) or maleic acid (or a salt thereof). Therefore, the technology of the invention is of great commercial value.

What is claimed is:

1. A method for isolating and purifying S-(1, 2-dicarboxyethyl)glutathione or a pharmacologically acceptable salt thereof from a reaction mixture available upon reacting glutathione or a salt thereof with either fumaric acid or a salt thereof or maleic acid or a salt thereof, which comprises a first step of converting the S-(1, 2-dicarboxyethyl) glutathione or salt thereof in said reaction mixture to the corresponding copper salt, dissolving the copper salt in an aqueous solution of acetic acid, formic acid or propionic acid, and removing the contaminant glutathione, oxidized glutathione and fumaric acid copper salts with the aid of activated carbon and a second step of dissolving or suspending the isolated S-(1, 2-dicarboxyethyl)glutathione copper salt in water and blowing hydrogen sulfide gas through the resulting aqueous solution or suspension to remove copper.

2. The method according to claim 1 wherein the activated carbon is used in a proportion of 5–20 w/w % with respect to said S-(1, 2-dicarboxyethyl)glutathione copper salt and the concentration of said aqueous solution of acetic acid, formic acid, or propionic acid is 1–50 v/v %.

* * * * *